(12) United States Patent
Kamath et al.

(10) Patent No.: US 7,142,635 B2
(45) Date of Patent: Nov. 28, 2006

(54) FIELD SPLITTING FOR INTENSITY MODULATED FIELDS OF LARGE SIZE

(75) Inventors: Srijit Kamath, Gainesville, FL (US); Sartaj Sahni, Gainesville, FL (US); Jonathan Gang Li, Gainesville, FL (US); Jatinder Palta, Gainesville, FL (US); Sanjay Ranka, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

(21) Appl. No.: 11/102,083

(22) Filed: Apr. 8, 2005

(65) Prior Publication Data

US 2005/0254623 A1   Nov. 17, 2005

Related U.S. Application Data

(60) Provisional application No. 60/616,025, filed on Oct. 5, 2004, provisional application No. 60/560,560, filed on Apr. 8, 2004.

(51) Int. Cl.
*A61N 5/10* (2006.01)
(52) U.S. Cl. ........................................... 378/65
(58) Field of Classification Search .................. 378/65
See application file for complete search history.

(56) References Cited

U.S. PATENT DOCUMENTS

| | | | |
|---|---|---|---|
| 5,724,403 A * | 3/1998 | Siochi et al. ............... 378/150 |
| 6,134,296 A * | 10/2000 | Siochi ........................... 378/65 |
| 6,335,961 B1 * | 1/2002 | Wofford et al. ............... 378/65 |
| 6,577,707 B1 * | 6/2003 | Siochi ........................... 378/65 |
| 6,661,871 B1 | 12/2003 | Siochi |
| 6,984,835 B1 * | 1/2006 | Harada ..................... 250/505.1 |
| 2005/0148841 A1 | 7/2005 | Kamath et al. |

OTHER PUBLICATIONS

Langer, Mark et al. "Improved leaf sequencing reduces segments or monitor units needed to deliver IMRT using multileaf collimators" Med. Phys. 28(12) Dec. 2001, pp. 2450-2458.*
Wu, Q. et al. "Dynamic splitting of large intensity-modulated fields", Phys. Med. Biol., 2000, 45:1731-1740.

* cited by examiner

*Primary Examiner*—Edward J. Glick
*Assistant Examiner*—Thomas R. Artman
(74) *Attorney, Agent, or Firm*—Akerman Senterfitt; Neil R. Jetter

(57) ABSTRACT

A method of delivering intensity modulated radiation therapy (IMRT) is disclosed. An intensity profile for the treatment of a patient is provided which spans a prescribed field width and includes a discrete profile having intensity values at each of a plurality of sample points bounded by the prescribed width. The prescribed width is compared to a maximum field width provided by the radiation treatment system. The intensity profile is split into a plurality of intensity profile portions, each having respective widths less than the maximum width if the prescribed width is greater than the maximum width. The prescribed field is also divided into a plurality of different profile portion split arrangements. A monitor unit (MU) efficiency is calculated for each of the arrangements. One of the arrangements is selected for delivery by the system using a leaf sequencing method.

15 Claims, 11 Drawing Sheets

FIELD SPLITTING FOR INTENSITY MODULATED FIELDS OF LARGE SIZE

CROSS-REFERENCE TO RELATED APPLICATIONS

This application claims the benefit of U.S. Provisional Application No. 60/560,560, filed Apr. 8, 2004; and U.S. Provisional Application No. 60/616,025, filed Oct. 5, 2004, which are incorporated herein by reference.

STATEMENT REGARDING FEDERALLY SPONSORED RESEARCH OR DEVELOPMENT

The United States Government may have certain rights to this invention pursuant to NIH Grant/Contract No. LM06659-03.

FIELD OF THE INVENTION

The invention relates to a radiation emitting device, and more particularly, to a system and method for efficiently and more safely delivering split radiation field treatment to a patient.

BACKGROUND

A radiation therapy device typically includes a radiation delivery device mounted to a gantry that is swiveled around a horizontal axis of rotation in the course of a radiation therapy treatment. The radiation delivery device generally delivers a high energy radiation beam. During treatment, the radiation beam is directed towards a patient lying in the isocenter of the gantry rotation.

The device thus normally includes a radiation source, such as a linear accelerator, for supplying the high energy radiation beam. The high energy radiation beam is typically an electron beam or X-ray beam.

To control the radiation emitted toward a given object, a beam shielding device, such as a plate arrangement or a collimator, is typically provided in the trajectory of the radiation beam between the radiation source and the patient. A collimator is a computer-controlled mechanical beam shielding device which generally includes multiple leaves, for example, a plurality of relatively thin plates or rods, typically arranged as opposing leaf pairs. The plates are formed from a relatively dense and radiation impervious material and are generally independently positionable to size and shape of the radiation beam. These leaves move over the tissue being radiated, thus blocking out some areas and filtering others to vary the beam intensity and precisely distribute the radiation dosage.

A multileaf collimator (MLC) is an example of a multileaf beam shielding device that can accurately and efficiently adjust the size and shape of the radiation beam. The size and shape of a radiation beam is designed during the treatment planning process. This is useful for both intensity modulated radiation treatment (IMRT) and three-dimensional conformal radiation therapy (3D CRT).

Traditional radiotherapy utilizes uniform beams of radiation, producing a uniform distribution of dose throughout the irradiated volume, which includes the target volume. This ensures the target is adequately covered, but does little or nothing to avoid often critical surrounding structures. With IMRT, the beams of radiation are made to be intentionally non-uniform. In this manner, the dose distribution can be shaped to reduce or eliminate radiation to surrounding structures. As a result, IMRT is increasingly used to treat large volumes because IMRT can deliver more conformal radiation while sparing the surrounding normal tissue.

Monitor unit (MU) efficiency is a commonly used measure of beam efficiency. MU efficiency is defined as the efficiency with which the incident radiation results in dose being in absorbed in the target region of a patient. A consequence of low MU efficiency is an increase in leakage radiation that reaches the surrounding (normal) tissue of the patient.

There are several components of a successful IMRT program. The first is a process referred to as "inverse planning." Inverse planning utilizes a mathematical algorithm to optimize the intensity of the various beams. This optimization process typically is highly computer intensive.

The second component is a process to convert the intensity distributions obtained, often referred to cumulatively as a fluence map, into a series of MLC leaf movements. This is referred to as "leaf sequencing." Many device-specific factors must be accounted for in this process. These factors include radiation leakage through and between the leaves, leaf speed, dose rate, and the "tongue-and-groove" effect.

IMRT can be performed either while the beam is on, which is referred to as dynamic multileaf collimator (DMLC) delivery, or by turning the beam off while the leaves move to their next position, which is referred to as segmented multileaf collimator (SMLC) delivery. The beam shielding device defines a field on the object to which a prescribed amount of radiation is to be delivered. The usual treatment field shape results in a three-dimensional treatment volume which includes segments of normal tissue, thereby limiting the dose that can be given to the target, such as a tumor. The dose delivered to the tumor can be increased, thereby decreasing the treatment time so that the amount of dose delivered to the normal surrounding tissue is decreased. Although current leaf sequencing algorithms have reduced somewhat the radiation level reaching surrounding normal tissue as compared to traditional uniform beams of radiation, these leaf sequences have not provided optimal MU efficiency.

Most IMRT treatments are administered with conventional MLC systems that are typically available on commercial linear accelerators. The MLC systems vary in design but each version has certain mechanical limitations, such as maximum leaf over-travel which limits the attainable width of the radiation beam.

It is sometimes necessary to expose large areas of the body of a patient to radiation. If the size of the required radiation field is too large relative to the maximum attainable width provided by the radiation delivery system, such as in the case of a large tumor, the entire radiation field cannot be exposed at one time by the radiation system. This necessitates that a large field be split into a plurality of abutting field portions, such as 2 or 3 fields portions, where the respective field portions are delivered one at a time.

The methods currently used for field splitting generally split the overall field into field portions having equal width. Thus, the width limitation problem is solved without regard to efficiency, and generally results in relatively poor monitor unit efficiency. This often results in longer delivery times, poor MU efficiency, and field matching problems.

Specifically, uncertainties in leaf and carriage positions have been reported to cause errors in the delivered dose (hot or cold spots) along the match line of the abutting field portions. Differences of up to 10% along the field split line when the split line crossed through the center of the target for all the fields has been observed.

Proposed solutions to the problem of dosimetric perturbation along the field split line include automatic feathering of split-fields by modifying the split line position for each gantry position or by dynamically changing radiation intensity in the overlap region of the split fields. However, none of the field splitting techniques reported have disclosed treatment delivery and MU efficiency optimization for split fields.

SUMMARY OF THE INVENTION

The invention is directed to a radiation delivery system and method which reduce the total monitor units (MUs) used to treat patients requiring large radiation fields. The phrase "large radiation field" is defined herein as a prescribed radiation field width determined by a dose optimization algorithm that exceeds the maximum attainable beam width provided by the radiation delivery system, such as the large field required, for example, in the treatment of certain neck and back tumors.

The invention includes leaf sequencing algorithms that as described herein automatically split a large radiation field into abutting or feathered field portions that can then be delivered one at a time so that the resulting treatment provides a MU efficiency which is higher as compared to conventional splitting techniques. Leaf sequencing algorithms determine various combinations of positions in which the radiation field can be split, and selects an allocation of widths of the respective field portions based on an optimization criteria. One optimization parameter is minimizing the total therapy time, and as a result the overall MU efficiency, the total therapy time being the sum of the optimal therapy times from each the resulting field portions.

Another optimizing parameter relates to optimizing segments. Each field portion is delivered using a leaf sequence. In any leaf sequence, when at least one leaf is moved from one position to a new position during treatment, thus changing the shape of the aperture, the segment is the to change. Thus, minimizing number of segments minimizes the number of "apertures'. Accordingly, optimization can be provided by minimizing the total number of segments used in leaf sequences of all field portions resulting from the split.

In the case of a SMLC, it is noted that the machine is off when at least one leaf needs to move to a new position. So the number of times the machine has to switch on/off will be the number of segments there are. For leaf sequencing in a single field, some regard the time needed to switch on\off should be taken into account. This switching time is reduced if number of segments reduces in leaf sequencing. Thus, what is minimized in this embodiment is the sum of the ON times over all segments and not the number of segments as this reduces leakage and other harmful effects of radiation (which are proportional to the ON time).

BRIEF DESCRIPTION OF THE DRAWINGS

A better understanding of the present invention can be obtained when the following detailed description is considered in conjunction with the following drawings in which:

FIG. 7 shows a tight upper bound for Lemma 4a.

DETAILED DESCRIPTION

Figure 1:
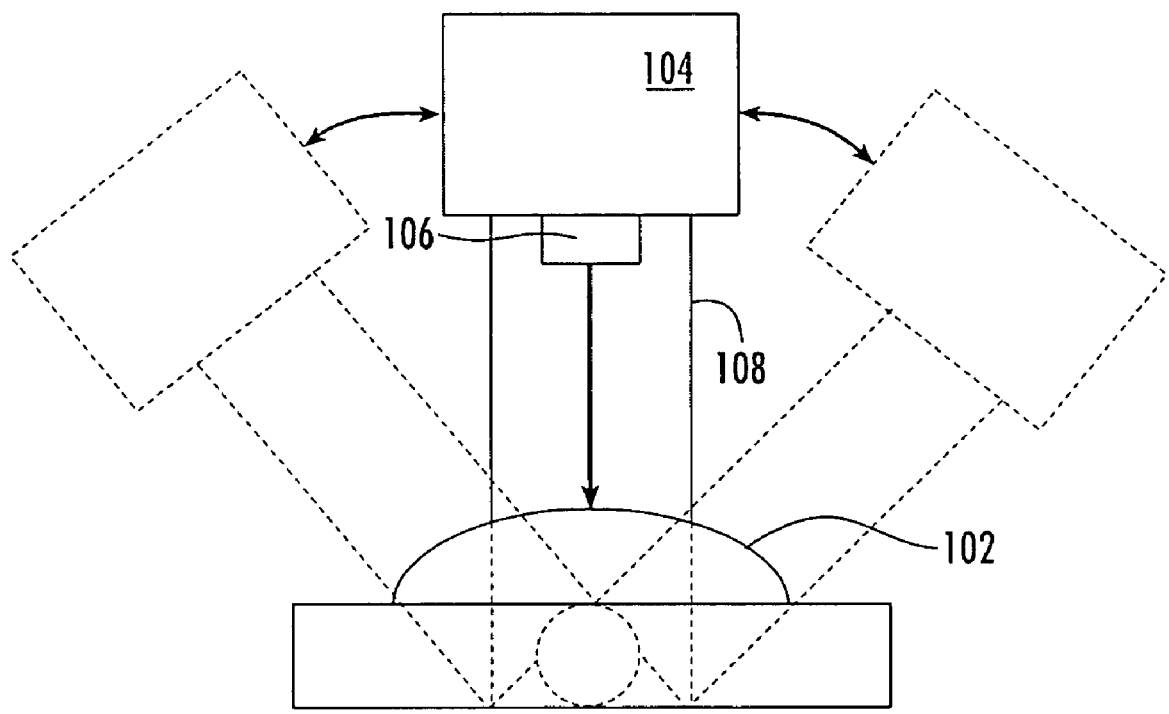
FIG. 1 is a schematic diagram of a system for delivering radiation treatment to a patient, according to one embodiment of the present invention.

FIG. 1 is a schematic diagram a system 100 for delivering radiation treatment to a patient 102, according to one embodiment of the present invention. The system 100 illustratively includes a radiation source 104 for providing a radiation beam and a beam-shaping device 106 interposed between the radiation source and the patient for shaping the radiation beam.

The radiation source 104, more particularly, can provide electron, photon, or other radiation useful for treating cancer or other disease. For example, as described in U.S. application Ser. No. 10/736,023 entitled "LEAF SEQUENCING METHOD AND SYSTEM" (U.S. Published Application Ser. No. 07/085,348) by the present inventors and incorporated herein in its entirety, the radiation source can be an electron accelerator for delivering an electron beam. As illustrated, the radiation source 104 is mounted upon a gantry 108 that rotates upon a fixed axis so as to permit the position of the radiation source to change relative to the patient 102.

Figure 2:
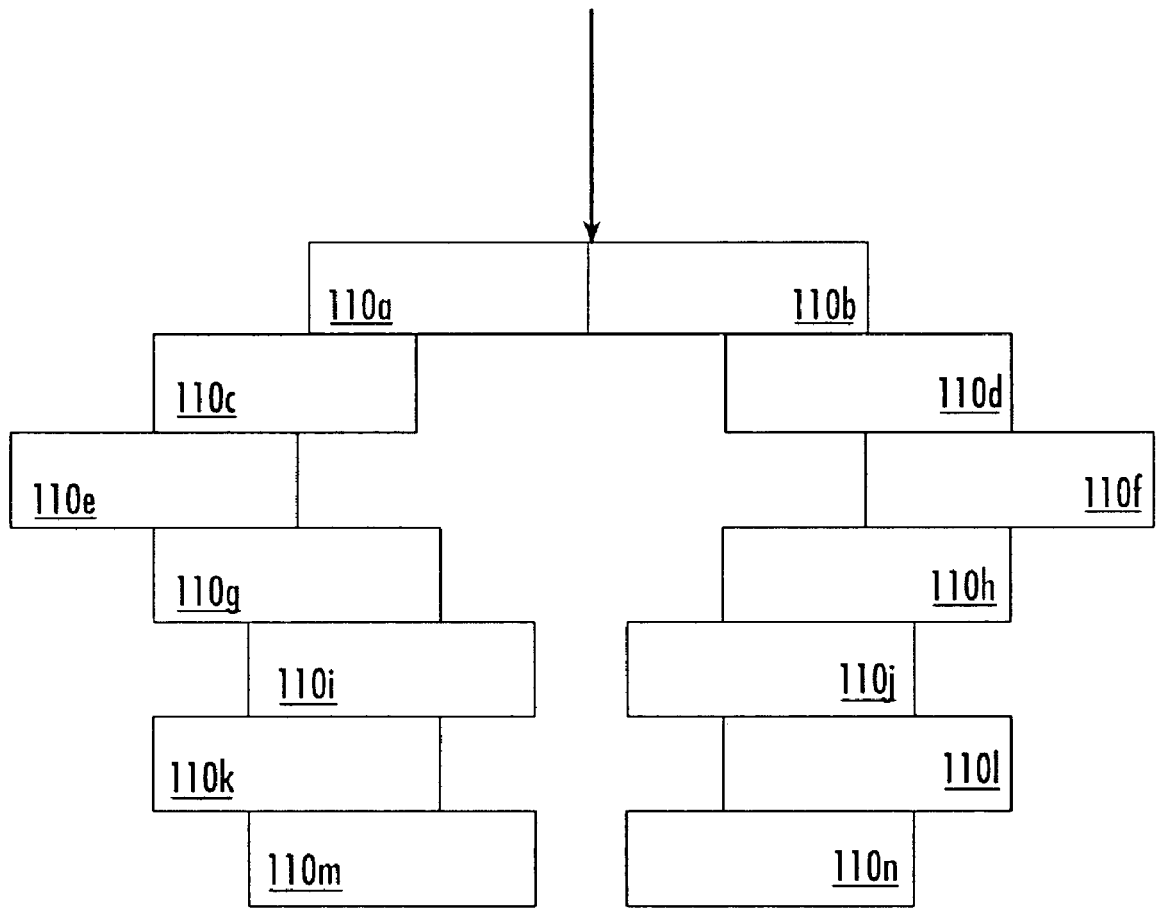
FIG. 2 is a schematic diagram of a beam-shaping device incorporated in a system for delivering radiation treatment to a patient, according to another embodiment of the present invention.

Referring additionally now to FIG. 2, the beam-shaping device 106 interposed between the radiation source 104 and the patient 102 illustratively comprises a plurality of opposing plates or leaves 110a–n that are substantially impervious to the radiation emitted by the radiation source. The leaves 110a–n can be moved by a drive unit (not shown) in a substantially horizontal motion relative to one another and substantially perpendicular to the radiation beam. The movement permits the plurality of leaves 110a–n to be aligned and realigned relative to one another and the radiation beam. Each such alignment comprises a leaf sequence that changes the size and shape of the radiation beam, as further described in U.S. application Ser. No. 10/736,023 incorporated herein. Accordingly, the leaf sequences determine the dimensions of a field on a designated region of the patient 102 to which a prescribed amount of radiation is to be delivered.

The beam-shaping device 106 can be an MLC. More particularly, the beam-shaping-device can comprise a segmented MLC. Alternatively, the beam-shaping device can comprise a dynamic MLC.

Figure 3:
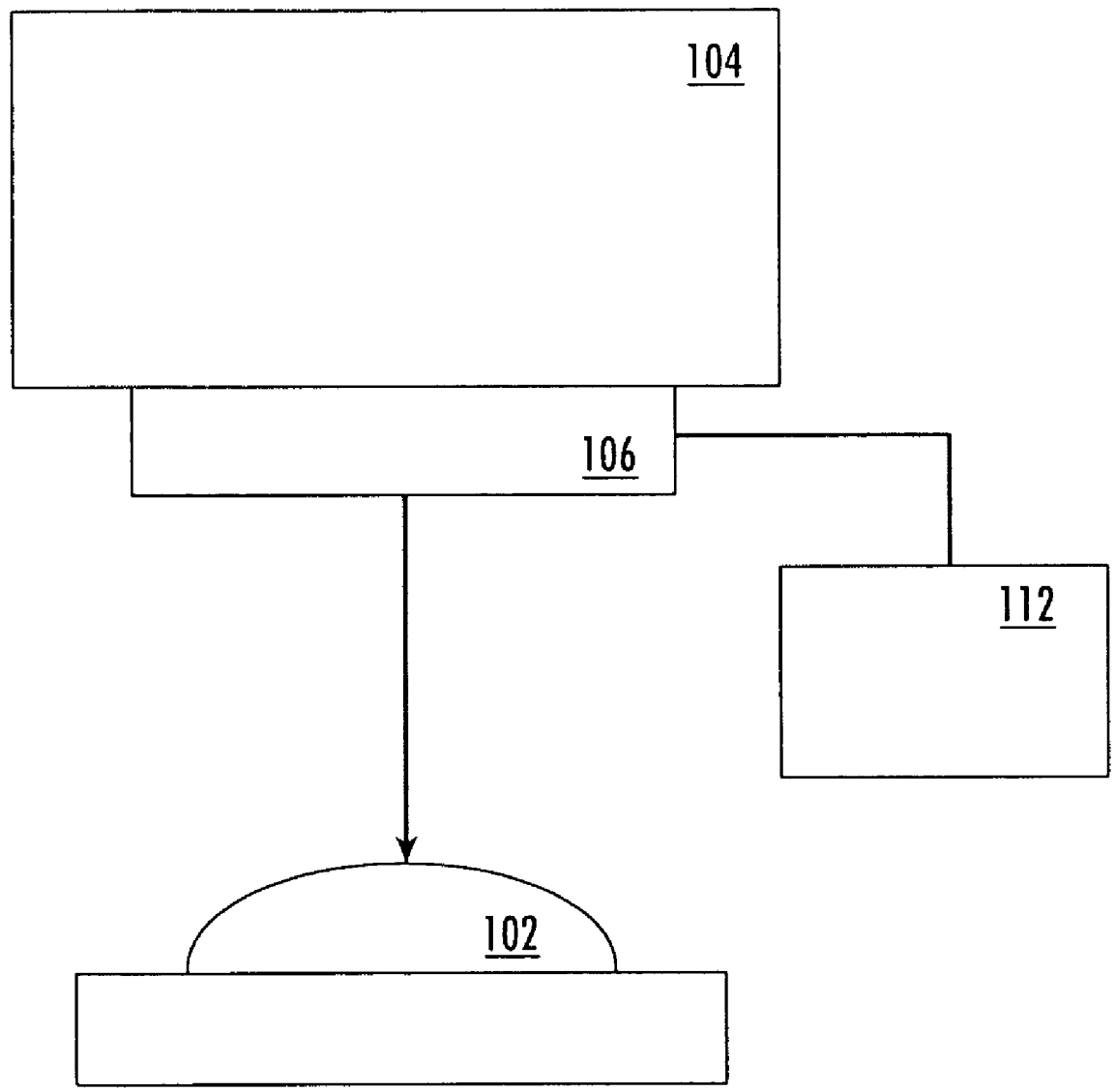
FIG. 3 is a schematic diagram of a system for delivering radiation treatment to a patient, according to still another embodiment of the present invention.

Referring additionally now to FIG. 3, the system 100 for delivering radiation treatment to a patient 102 illustratively includes a. processor in communication with the beam-shaping device 106. As described herein, the processor 112 can control the beam-shaping device 106 so that the beam-shaping device splits the radiation beam into a plurality of radiation fields that are delivered to the patient. The radiation beam, more particularly, is split so as to substantially minimize at least one of a total therapy time and a total number of leaf sequences in delivering a predetermined dosage of radiation to the patient. As defined herein, a substantial minimization of the total therapy time denotes a reduction of the therapy time to no more 20 percent, and more preferably no more than 10 percent, over an absolute minimum. Similarly, minimization of the total number of leaf sequences denotes no more than 20 percent, and more preferably no more than 10 percent, over the absolute minimum.

According to one embodiment, the processor 112 can connect to a standard input-output (I/O) device such as a keyboard. Thus, the processor can be programmed, for example, by a therapist according to instructions dictated by an oncologist. According to still another embodiment, the processor 112 can controls 112 the beam-shaping device 106 by executing and delivering instructions to the drive units (not shown) that align the opposing plates or leaves 110a–n so that different leaf sequences are effected according to the programmed instructions.

Figure 4:
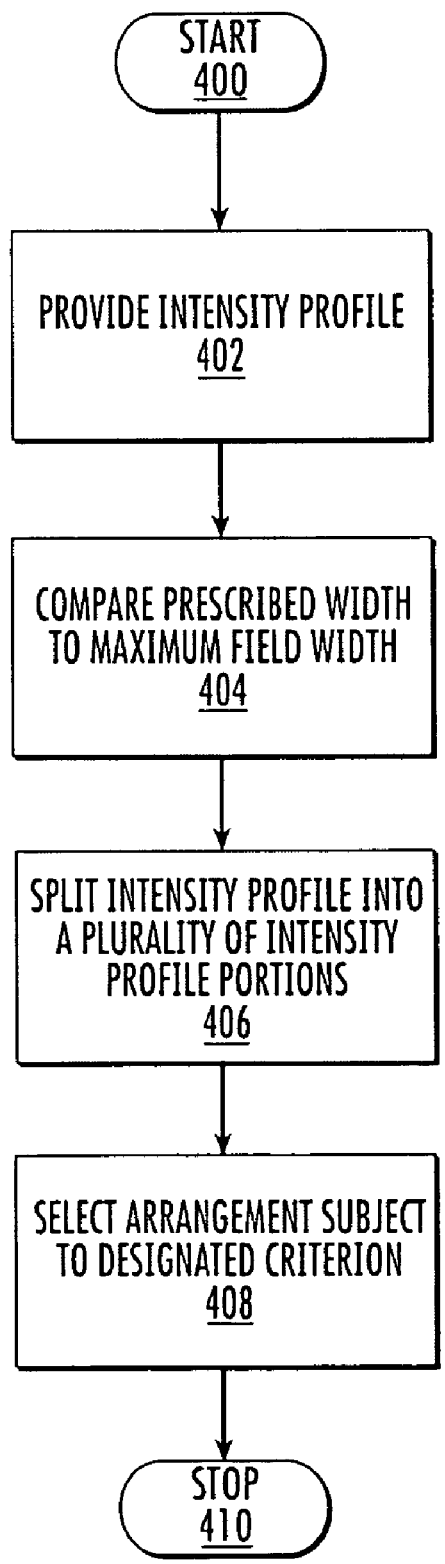
FIG. 4 is a flowchart of a method of delivering radiation treatment to a patient, according to an embodiment of the invention.

FIG. 4 is a flowchart illustrating the method 400 of delivering radiation to a patient, the radiation delivery defining an intensity-modulated radiation therapy (IMRT) as will be readily appreciated by one of ordinary skill in the art. The method 400 illustratively includes at step 402 providing an intensity profile for the treatment of a patient, wherein the intensity profile spans a prescribed field width and comprises a discrete profile having intensity values at each of a plurality of sample points bounded by the prescribed width. The method 400 further illustratively includes, at step 404, comparing the prescribed width to a maximum field width provided by a radiation treatment system.

At step 406, the method 400 proceeds with the splitting of the intensity profile into a plurality of intensity profile portions, each having respective widths less than the maximum width if the prescribed width is greater than the maximum width. The splitting, moreover, also illustratively includes dividing the prescribed field into a plurality of different profile portion split arrangements and calculating a monitor unit (MU) efficiency for each of the plurality of arrangements. The method illustratively includes, at step 408, selecting one of the arrangements for delivery by the system using a leaf sequencing method.

EXAMPLES

A general example of radiation field splitting according to the invention is now presented. In the case of a 14.5 cm width limitation for the radiation beam delivered by the radiation source 104, a required 20 cm wide field may be split into two field portions less than 14.5 cm. For example, one portion can be one-third the original field (6.6 cm) and the other portion can be two-thirds (13.4 cm) of the required field width.

The method thus examines different ratios in which a large field may be split in a feasible manner, analyzes the efficiency of each option relative to one or more criteria, and determines the best option. The option selected is then implemented and the radiation therapy is delivered to the patient pursuant to the radiation split.

Leaf sequencing algorithms that are optimal for MU efficiency while satisfying hardware constraints have been disclosed in U.S. application Ser. No. 10/736,023 entitled "LEAF SEQUENCING METHOD AND SYSTEM" (U.S. Published Application Ser. No. 07/085,348) by the present inventors, which as stated above is incorporated herein in its entirety. Such leaf sequencing algorithms are optimal for single radiation fields. The optimal field splitting algorithms may by used for each of the plurality of split field portions to optimally account for interdigitation and tongue-and-groove effect generated by conventional multileaf collimators.

Optimal field splitting for a single leaf pair is first presented. Although a radiation system having a single leaf pair is not a practical radiation therapy system, the field splitting solution obtained relative to such a system can form the basis for optimum field splitting solutions for a practical multi-leaf radiation system.

The delivery of the intensity map produced by the optimizer is first considered. The intensity map from the optimizer is a discrete matrix. The spatial resolution of this matrix is similar to the smallest beamlet size. The beamlet size typically ranges from about 5–10 mm.

$I(x)$ is the desired intensity profile along x axis. The discretized profile illustratively delivered by the processor 112 gives the intensity values at sample points $x_1, x_2, \ldots, x_m$. It is assumed that the sample points are uniformly spaced and that $\Delta x = x_{i+1} - x_i$, $1 \leq i < m$. $I(x)$ is assigned the value $I(x_i)$ for $x_i \leq x < x_i + \Delta x$, $1 \leq i \leq m$. Now, $I(x_i)$ is the desired intensity profile, i.e., $I(x_i)$ is a measure of the number of MUs for which $x_i$, $1 \leq i \leq m$, needs to be exposed. In the remainder of this application, the profile $I(x_i)$ is referred to as I.

Figure 5:
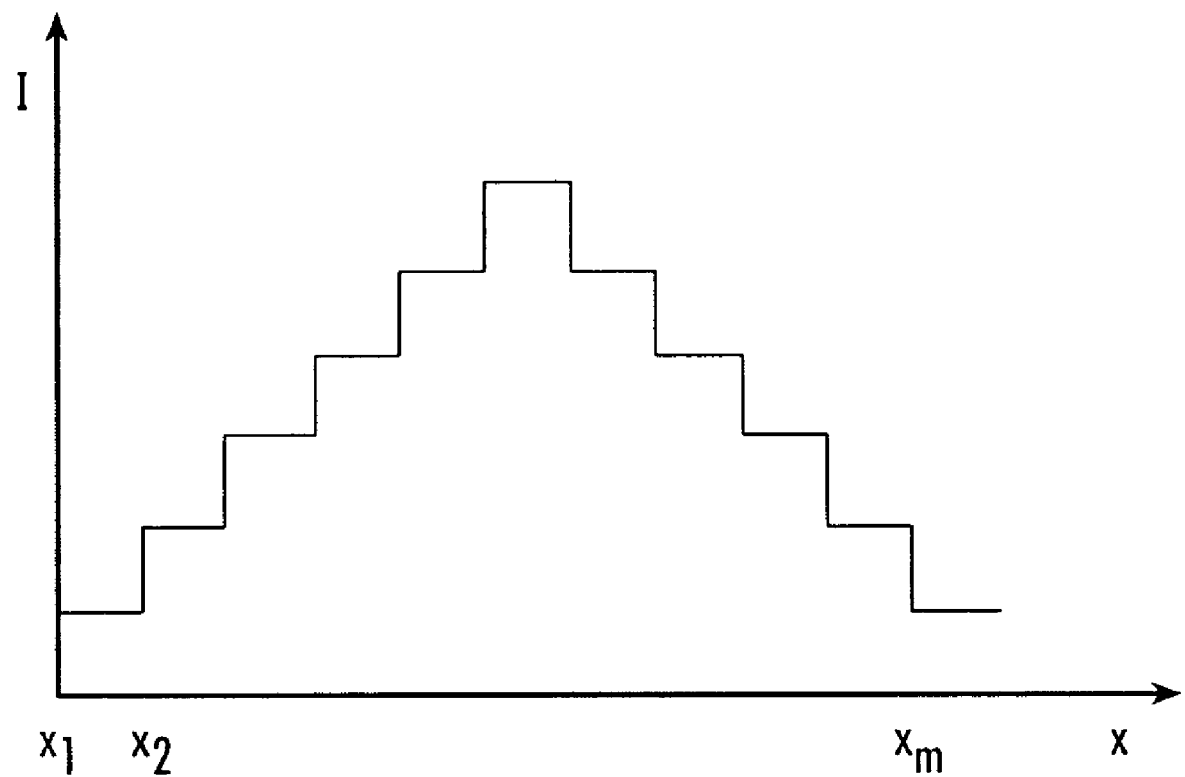
FIG. 5 shows an exemplary intensity profile generated, according to yet another embodiment of the present invention.

FIG. 5 shows a profile, which corresponds to the discrete sample points $x_1, x_2, \ldots, x_m$. This profile can be delivered either with the Segmental Multileaf Collimation (SMLC) method or with a Dynamic Multileaf Collimation (DMLC). This description describes the invention in terms of a SMLC, although those having ordinary skill in the art will recognize the invention is in no way limited to SMLC and can be applied to DMLC systems without modification.

Delivering a profile using one field for a single leaf pair is first now considered. Firstly, I is designated as the desired intensity profile. The optimal therapy time for I is given by the following lemma.

Lemma 1. Let inc1, inc2, ..., incq be the indices of the points at which $I(x_i)$ increases, i.e., $I(x_{inci}) > I(x_{inci-1})$. The therapy time for the plan $(I_l, I_r)$ generated by Algorithm SINGLEPAIR disclosed in application Ser. No. 10/736,023 is $\Sigma_{i=1}^{q}[I(x_{inci}) - I(x_{inci-1})]$, where $I(x_{inc1-1}) = 0$. Algorithm SINGLEPAIR, which can be implemented by the processor 112, can be directly used to obtain plans when I is deliverable using a single field. Let l be the least index such that $I(x_l) > 0$ and let g be the greatest index such that $I(x_g) > 0$. Without loss of generality, the processor 112 can set l=1. Thus, the width of the profile is g sample points, where g can vary for different profiles. Assuming that the maximum allowable field width is w sample points, I is deliverable using one field if $g \leq w$; I requires at least two fields for $g > w$; I requires at least three fields for $g > 2w$. The case where $g > 3w$ is not considered herein as it does not typically arise in clinical cases. However, if more than three field portions are required, the optimum field solution can be easily derived for such a situation by one having ordinary skill in the art based on the solutions to the various field portion cases described above.

The objective of field splitting directed with the processor 112 configured to run the algorithms described herein is to split a profile so that each of the resulting profiles is deliverable using a single field. Further, it is desirable that the total therapy time is minimized, so that the sum of optimal therapy times of the resulting field portions is minimized. The problem of splitting the profile I of a single leaf pair into 2 profiles each of which is deliverable from the radiation source 104 using one field such that the sum of their optimal therapy times is minimized will be referred to herein as the S2 (single pair 2 field split) problem. The sum of the optimal therapy times of the two resulting profiles is denoted by S2 (I). S3 and S3(I) are defined similarly for splits into 3 profiles.

An S1 problem does not necessitate splitting the input profile, which is to be delivered using a single field. Note that S1(I) is the optimal therapy time for delivering the profile I in a single field. This follows from Lemma 1, above, and the fact that the plan generated using Algorithm SINGLEPAIR is optimal in therapy time, $S1(I)=\Sum_{i=1}^{q}[I(x_{inci})-I(x_{inci-1})]$.

Splitting a profile into two field portions with a single leaf pair is now considered. Suppose that a profile I is split into two profiles. Let j be the index at which the profile is split. As a result, two profiles are obtained, $P_j$ and $S_j$. $P_j(x_i)=I(x_i)$, $1 \leq i < j$, and $P_j(x_i)=0$, elsewhere. $S_j(x_i)=I(x_i)$, $j \leq i \leq g$, and $S_j(x_i)=0$, elsewhere. $P_j$ is a prefix profile and $S_j$ is a suffix profile of I.

Lemma 2. Let $S1(P_j)$ and $S1(S_j)$ be the optimal therapy times, respectively, for $P_j$ and $S_j$. Then $S1(P_j)+S1(S_j)=S1(I)+\hat{I}(x_j)$, where $\hat{I}(x_j)=\min\{I(x_{j-1}),I(x_j)\}$. From Lemma 1, $S1(I)=\Sum_{i=1}^{q}[I(x_{inci})-I(x_{inci-1})]$. For the prefix profile, $S1(P_j)=\Sum_{inci<j}[I(x_{inci})-I(x_{inci-1})]$. The optimal therapy time of the suffix profile $S_j$ is equal to the sum of the increments in the intensities of successive sample points of the suffix profile. Adding these increments results in, $S1(S_j)=S_j(x_j)-S_j(x_{j-1})+\Sum_{inci>j}[I(x_{inci})-I(x_{inci-1})]=I(x_j)+\Sum_{inci>j}[I(x_{inci})-I(x_{inci-1})]$ (since $S_j(x_{j-1})=0$ and $S_j(x_j)=I(x_j)$). If $I(x_j)>I(x_{j-1})$, this can be written as $S1(S_j)=(I(x_j)-I(x_{j-1}))+\Sum_{inci>j}[I(x_{inci})-I(x_{inci-1})]+I(x_{j-1})=\Sum_{inci \geq j}[I(x_{inci})-I(x_{inci-1})]+I(x_{j-1})$ If $I(x_j) \leq I(x_{j-1})$, $S1(S_j)=\Sum_{inci>j}[I(x_{inci})-I(x_{inci-1})]+I(x_j)=\Sum_{inci \geq j}[I(x_{inci})-I(x_{inci-1})]+I(x_j)$. Therefore $S1(S_j)=\Sum_{inci \geq j}[I(x_{inci})-I(x_{inci-1})]+\min\{I(x_{j-1}),I(x_j)\}$. By addition, $S1(P_j)+S1(S_j)=\Sum_{i=1}^{q}[I(x_{inci})-I(x_{inci-1})]+\min\{I(x_{j-1}),I(x_j)\}=S1(I)+\hat{I}(x_j)$.

Figure 6:
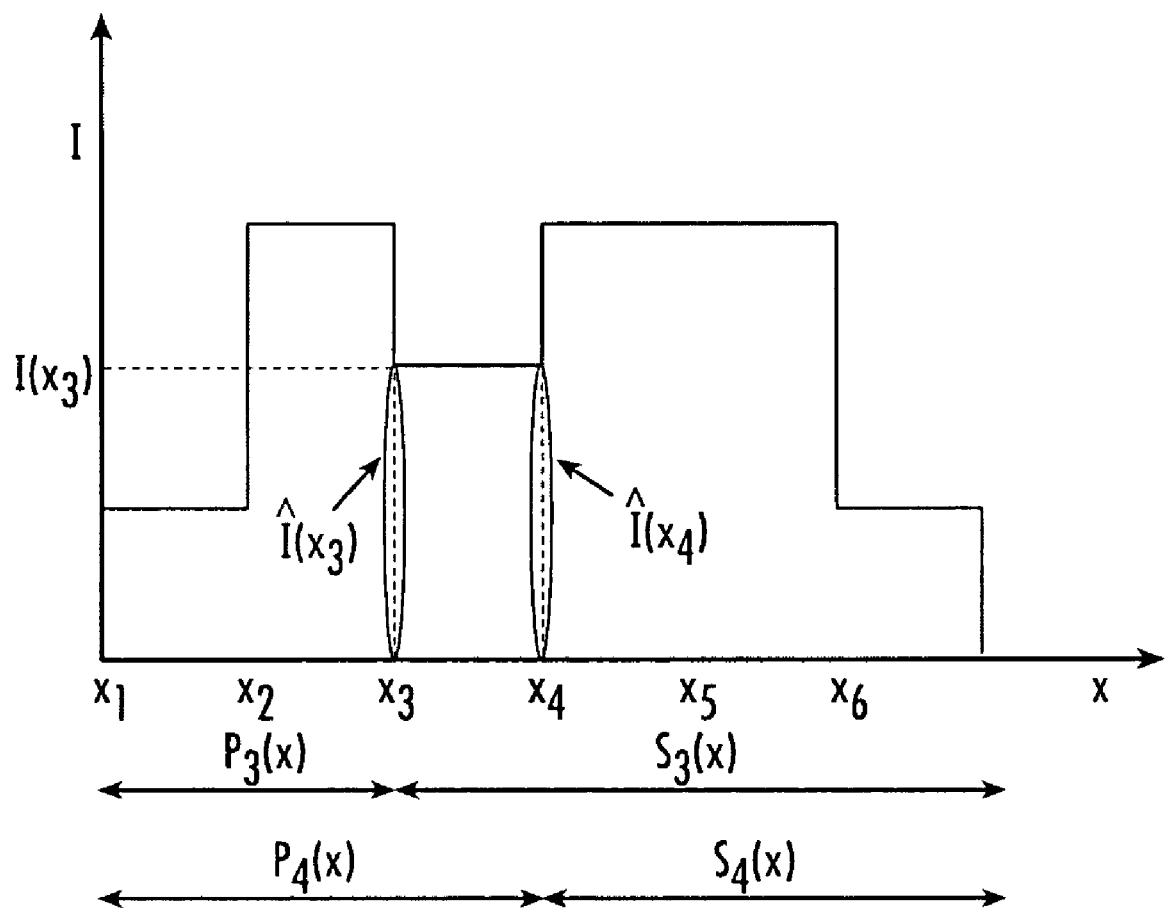
FIG. 6 shows splitting of a profile into two field portions, according to still another embodiment of the present invention.

Lemma 2 is illustrated in FIG. 6. The optimal therapy time for the profile I is the sum of increments in intensity values of successive sample points. However, if I is split at $x_3$ into $P_3$ and $S_3$, an additional therapy time of $\hat{I}(x_3)=\min\{I(x_2),I(x_3)\}=I(x_3)$ is required for treatment. Similarly, if I is split at $x_4$ into $P_4$ and $S_4$, an additional therapy time of $\hat{I}(x_4)=\min\{I(x_3),I(x_4)\}=I(x_3)$ is required.

Splitting a profile into two is now considered. Lemma 2 leads to the following O(g) algorithm, defined herein as Algorithm S2.

Algorithm S2
Compute $\hat{I}(x_i)=\min\{I(x_{i-1}),I(x_i)\}$, for $g-w<i \leq w+1$.
Split the field at a point $x_j$ where $\hat{I}(x_j)$ is minimized for $g-w<j \leq w+1$.

It is evident from Lemma 2 that if the width of the profile is less than the maximum allowable field width ($g \leq w$), the profile is best delivered using a single field. If g>2w two fields are clearly insufficient. Accordingly, it is useful to apply Algorithm S2 only for $w<g \leq 2w$. Once the profile I is split into two as determined by Algorithm S2, the prefix and suffix profiles are delivered using separate fields. The total therapy time is $S2(I)=S1(P_j)+S1(S_j)$, where j is the split point.

Splitting a profile into three field portions a single leaf pair is now considered. Suppose that a profile I is split into three profiles. Let j and k, j<k, be the indices at which the profile is split. As a result, three profiles $P_j$, $M_{(j,k)}$ and $S_k$ result, where $P_j(x_i)=I(x_i)$, $1 \leq i<j$, $M_{(j,k)}(x_i)=I(x_i)$, $j \leq i<k$, and $S_k(x_i)=I(x_i)$, $k \leq i \leq g$. $P_j$, $M_{(j,k)}$ and $S_k$ are zero at all other points. $P_j$ is a prefix profile, $M_{(j,k)}$ is a middle profile of I and $S_k$ is a suffix profile.

Lemma 3. Let $S1(P_j)$, $S1(M_{(j,k)})$ and $S1(S_k)$ be the optimal therapy times, respectively, for $P_j$, $M_{(j,k)}$ and $S_k$. Then $S1(P_j)+S1(M_{(j,k)})+S1(S_k)=S1(I)+\min\{I(x_{j-1}),I(x_j)\}+\min\{I(x_{k-1}),I(x_k)\}=S1(I)+\hat{I}(x_j)+\hat{I}(x_k)$ Similar to that of Lemma 2, Lemma 3 motivates the following algorithm for S3, defined herein as Algorithm S3:

Algorithm S3
Compute $\hat{I}(x_i)=\min\{I(x_{i-1}),I(x_i)\}$, for $1<i \leq w+1$, $g-w<i \leq g$.
Split the field at two points $x_j$, $x_k$ such that $1 \leq j \leq w+1$, $g-w<k \leq g$, $0<k-j \leq w$, and $\hat{I}(x_j)+\hat{I}(x_k)$ is minimized.

Note that for Algorithm S3 to split I into three profiles that are each deliverable in one field, it must be the case that $g \leq 3w$. Once the profile I is split into three as determined by Algorithm S3, the resulting profiles are delivered using separate fields. The minimum total therapy time is $S3(I)=S1(P_j)+S1(M_{(j,k)})+S1(S_k)$. Algorithm S3 examines at most $g^2$ candidates for (j,k). So the complexity of the algorithm is $O(g^2)$.

Bounds on optimal therapy time ratios are now considered. The following bounds on ratios of optimal therapy times are now proven.

Figure 7:
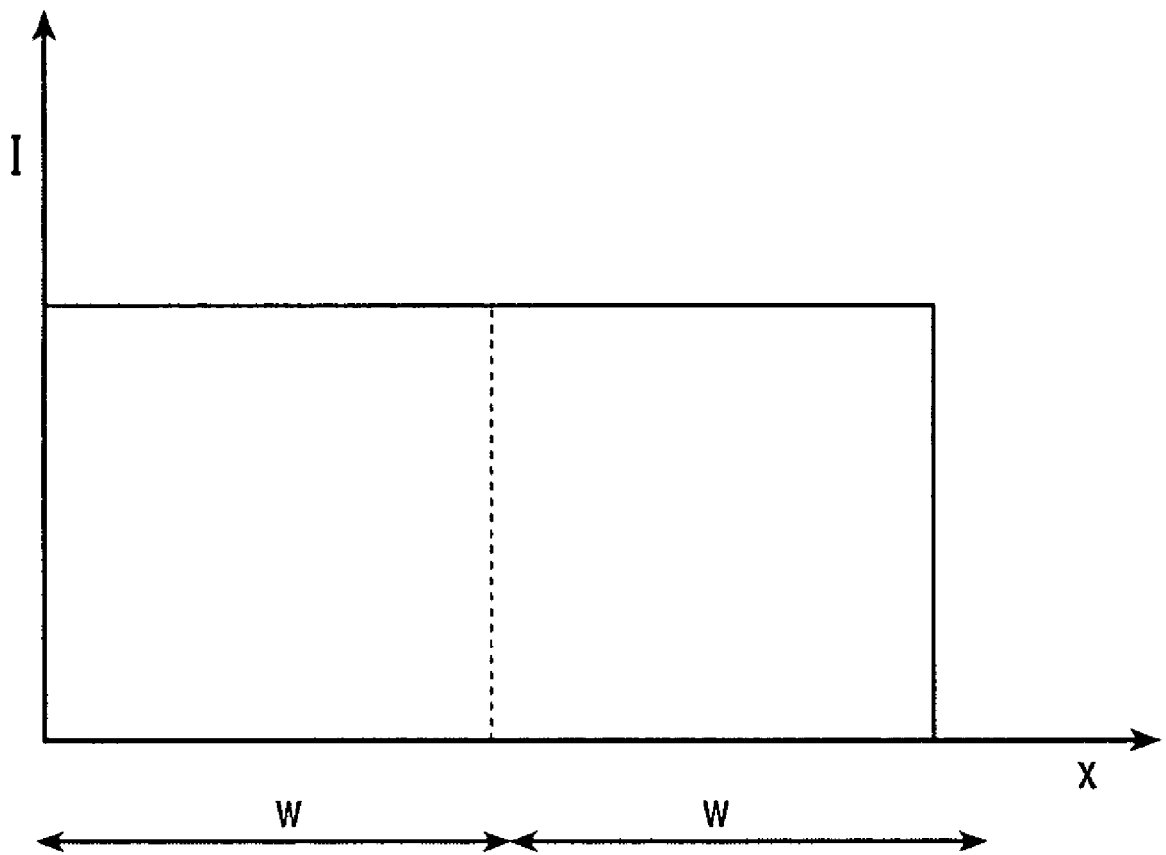

Lemma 4.
$1 \leq S2(I)/S1(I) \leq 2$
$1 \leq S3(I)/S1(I) \leq 3$
$0.5 < S3(I)/S2(I) < 2$ $S2(I)=\Sum_{i=1}^{q}[I(x_{inci})-I(x_{inci-1})]+\min\{I(x_{j-1}),I(x_j)\}=S1(I)+\min\{I(x_{j-1}),I(x_j)\}$, where j is the optimum point determined by the algorithm to split the field as determined by Algorithm S2. This implies $S2(I)/S1(I) \geq 1$ and so splitting a field into two portions never improves optimal therapy time. For an upper bound on the ratio, note that $S1(I) \geq \min\{I(x_{j-1}),I(x_j)\}$ since at least $\min\{I(x_{j-1}),I(x_j)\}$ MUs are required to deliver I. So $S2(I) \leq 2*S1(I)$. The example of FIG. 7 shows that the upper bound is tight. The profile I has 2w sample points, i.e., it has a width $2w\Delta x$. So it has to be split exactly at $x_{w+1}$. The resulting prefix and suffix profiles each have an optimal therapy time equal to that of I.

Figure 8:
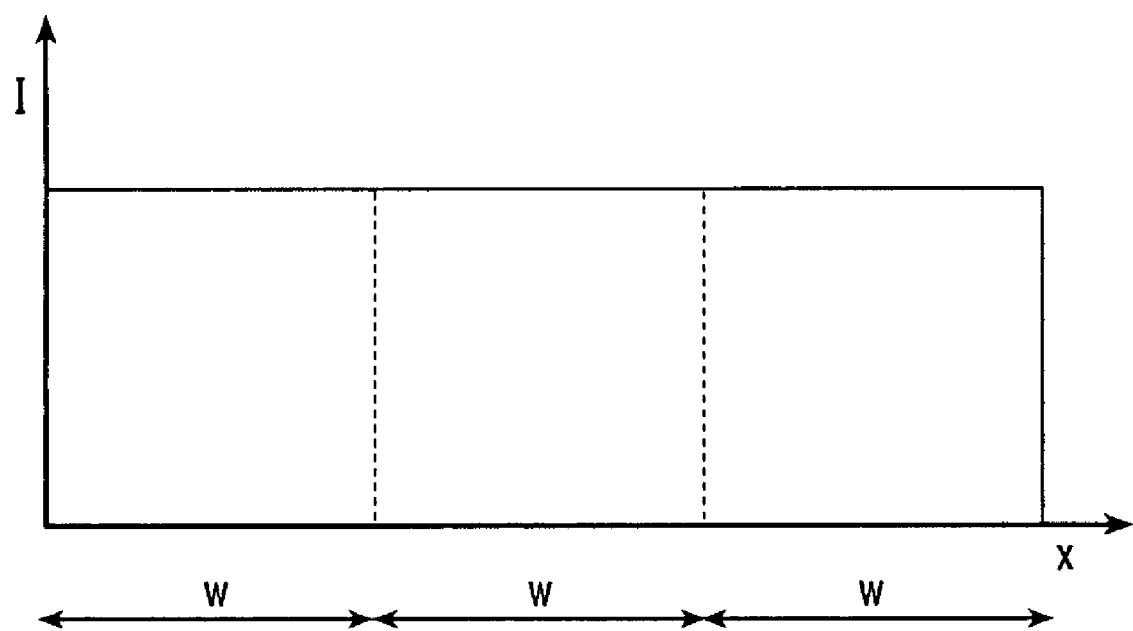
FIG. 8 shows a tight upper bound for Lemma 4b.

$S3(I)=S1(I)+\min\{I(x_{j-1}),I(x_j)\}+\min\{I(x_{k-1}),I(x_k)\}$ where j and k are as in Algorithm S3. Clearly, $S3(I)/S1(I) \geq 1$. Also, $S1(I) \geq \min\{I(x_{j-1}),I(x_j)\}$ and $S1(I) \geq \min\{I(x_{k-1}),I(x_k)\}$. Therefore, $S2(I)<3*S1(I)$. Once again the upper bound is tight as shown in the FIG. 8. The profile shown has width $3w\Delta x$ and needs to be split at $x_{w+1}$ and at $x_{2w+1}$. Each of the resulting profiles has optimal therapy time equal to S1(I).

Figure 9:
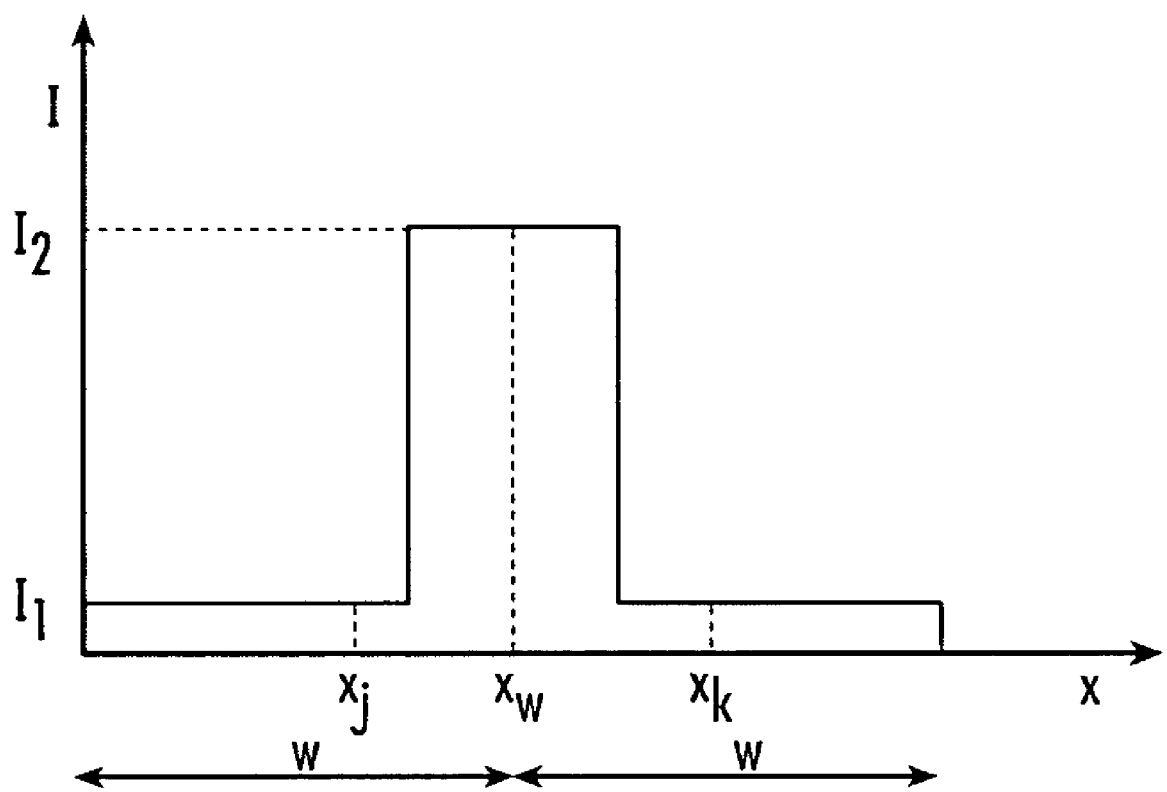
FIG. 9 shows a tight lower bound for Lemma 4c.

From above, $S3(I) \geq S1(I)$ and $S2(I) \leq 2*S1(I)$. So $S3(I)/S2(I) \geq 0.5$. $S3(I)/S2(I)=0.5$ only if $S3(I)=S1(I)$ and $S2(I)=2*S1(I)$. Suppose that $S3(I)=S1(I)$. Then there exist indices j,k such that $\min\{I(x_{j-1}),I(x_j)\}+\min\{I(x_{k-1}),I(x_k)\}=0$, i.e., $\min\{I(x_{j-1}),I(x_j)\}=0$ and $\min\{I(x_{k-1}),I(x_k)\}=0$. This and the fact that $I(x_j) \neq 0, I(x_g) \neq 0$ implies that the profile has at least two disjoint components separated by a sample point at which the desired intensity is zero. Sample points in the two disjoint components cannot be exposed at the same time and so there does not exist a point $x_i$ such that $I(x_i)=S1(I)$. So $S2(I)=S1(I)+\min_{g-w<i \leq g}\min\{I(x_{i-1}),I(x_i)\}<2*S1(I)$. It follows that $S3(I)/S2(I)>0.5$. FIG. 9 shows an example where the ratio can be made arbitrarily close to 0.5. In this example, $S1(I)=I_2$. The profile has a width of $2w\Delta x$ and therefore needs to be split at $x_{w+1}$. The resulting profiles each have an optimal therapy time of S1(I) so that S2 (I)=2*S1(I). S3(I)=S1(I)+2I$_1$ and so S3(I)→S1(I) as I$_1$→0.

Figure 10:
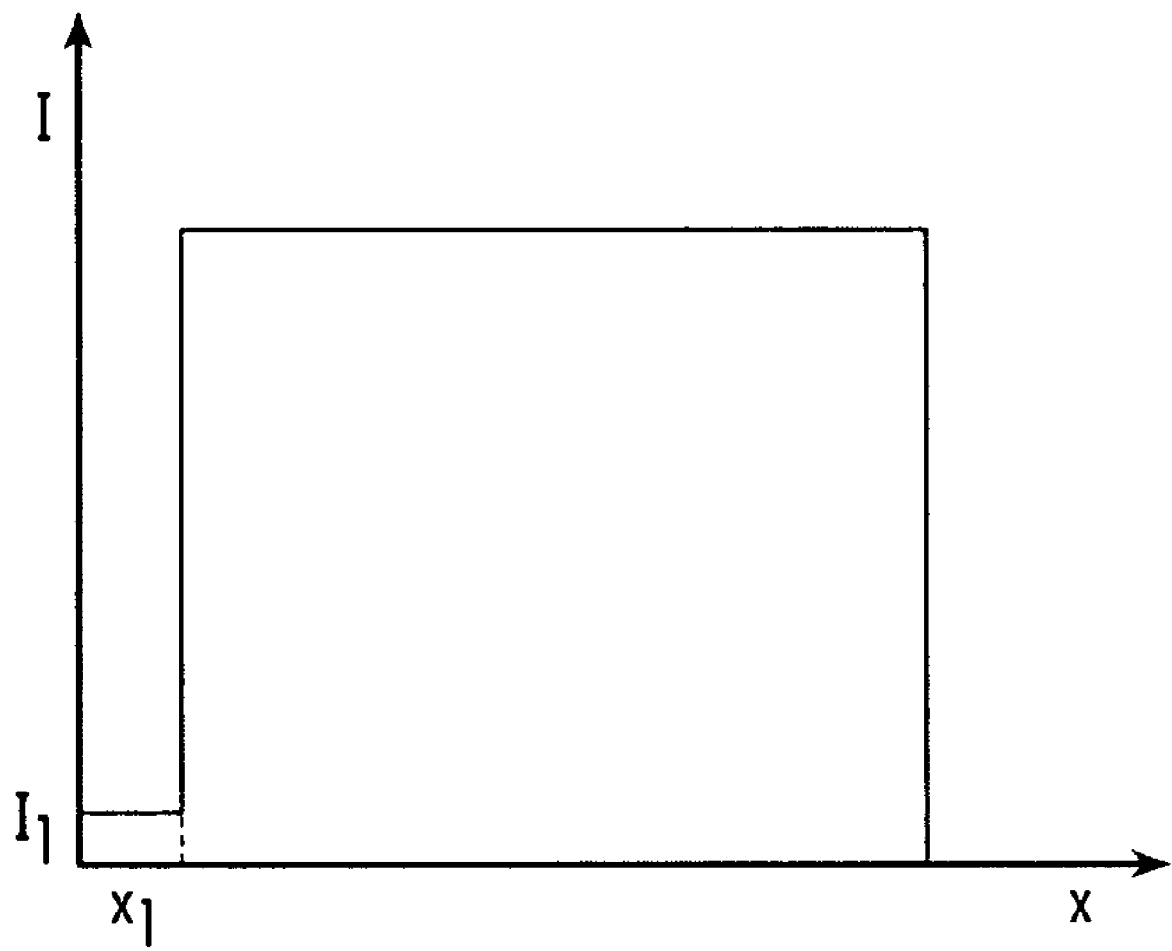
FIG. 10 shows a tight upper bound for Lemma 4d.

To obtain an upper bound note that the best split point for S2 (say $x_j$) is always a permissible split point for S3. By selecting this as one of the two split points for S3, a split into three field portions can be constructed such that the total therapy time of profiles resulting from this split is S2 (I)+min{I($x_{k-1}$),I($x_k$)}, where k is the second split point defining that split. Since min{I($x_{k-1}$),I($x_k$)}≦S1(I)≦S2 (I), the total therapy time of the split ≦2*S2 (I). So S3(I)/S2 (I)≦2. The ratio can be arbitrarily close to 2 as demonstrated in FIG. 10. One can verify that for the profile I in this example, S3(I)/S2 (I)→2 as I$_1$→0.

Optimal field splitting for multiple leaf pairs is now considered. The input intensity matrix (say I) for the leaf sequencing problem is obtained using the well known inverse planning technique. The matrix I consists of n rows and m columns. Each row of the matrix specifies the number of monitor units (MUs) that need to be delivered using one leaf pair. Denote the rows of I by $I_1, I_2, \ldots, I_n$.

For the case where I is deliverable using one field, the leaf sequencing problem has been optimized in the past by the inventors as described in U.S. application Ser. No. 10/736,023 incorporated herein in its entirety. The algorithm that generates optimal therapy time schedules for multiple leaf pairs, designated herein as Algorithm MULTIPAIR, applies algorithm SINGLEPAIR independently to each row $I_i$ of I. Without loss of generality it is assumed that the least column index containing a non zero element in I is 1 and the largest column index containing a non zero element in I is g. If g>w, the profile will need to be split. The problems M1, M2 and M3 are defined for multiple leaf pairs as being analogous to S1, S2 and S3 for single leaf pair. The optimal therapy times M1(I), M2(I) and M3(I) are also defined similarly.

Splitting a profile into two field portions is now considered for the case of multiple leaf pair. Suppose that a profile I is split into two profiles. Let $x_j$ be the column at which the profile is split. This is equivalent to splitting each row profile $I_i$, 1≦i≦n, at j as defined for single leaf pair split. As a result two profiles are obtained, $P_j$ (prefix) and $S_j$ (suffix). $P_j$ has rows $P_j^1, P_j^2, \ldots, P_j^n$ and $S_j$ has rows $S_j^1, S_j^2, \ldots, S_j^n$.

Lemma 5. Suppose I is split into two profiles at $x_j$. The optimal therapy time for delivering $P_j$ and $S_j$ using separate fields is max$_i$\{S1($P_j^i$)\}+max$_i$\{S1 ($S_j^i$)\}.

The optimal therapy time schedule for $P_j$ and $S_j$ are obtained using Algorithm MULTIPAIR. The therapy times are max$_i$\{S1($P_j^i$)\} and max$_i$\{S1($S_j^i$)\} respectively. So the total therapy time is max$_i$\{S1($P_j^i$)\}+max$_i$\{S1($S_j^i$)\}. From Lemma 5 it follows that the M2 problem can be solved by finding the index j, 1<j≦g such that max$_i$\{S1($P_j^i$)\}+max$_i$\{S1 ($S_j^i$)\} is minimized according to an M2 procedure defined by the algorithm designated herein as Algorithm M2:

Algorithm M2:
Compute max$_i$\{S1($P_j^i$)\}+max$_i$\{S1($S_j^i$)\} for g−w<j≦w+1.
Split the field at a point $x_j$ where max$_i$\{S1($P_j^i$)\}+max$_i$\{S1 ($S_j^i$)\} is minimized for g−w<j≦w+1.

From Lemma 1, S1($P_j^i$)=$\Sigma_{inci\leq j}$[I($x_{inci}$)−I($x_{inci-1}$)]. For each i, S1($P_1^i$), S1($P_2^i$), ..., S1($P_g^i$) can all be computed in a total of O(g) time progressively from left to right. So the computation of S1s (optimal therapy times) of all prefixes of all n rows of I can be done in O(ng) time. The same is true of suffixes. Once these values are computed, step (1) of Algorithm M2 is applied. max$_i$\{S1($P_j^i$)\}+max$_i$\{S1($S_j^i$)\} can be found in O(n) time for each j and hence in O(ng) time for all j in the permissible range. So the time complexity of Algorithm M2 is O(ng).

Splitting a profile into three field portions is now considered for the case of multiple leaf pair. Suppose that a profile I is split into three profiles. Let j, k, j<k, be the indices at which the profile is split. Once again, this is equivalent to splitting each row profile $I_i$, 1≦i≦n at j and k as defined for single leaf pair split. As a result, three profiles $P_j$, $M_{(j,k)}$ and $S_k$ result. $P_j$ has rows $P_j^1, P_j^2, \ldots, P_j^n$, $M_{(j,k)}$ has rows $M_{(j,k)}^1$, $M_{(j,k)}^2, \ldots, M_{(j,k)}^n$ and $S_k$ has rows $S_k^1, S_k^2, \ldots, S_k^n$.

Lemma 6. Suppose I is split into three profiles by splitting at $x_j$ and $x_k$, j<k. The optimal therapy time for delivering $P_j$, $M_{(j,k)}$ and $S_k$ using separate fields is max$_i$\{S1($P_j^i$)\}+max$_i$\{S1 ($M_{(j,k)}^i$)\}+max$_i$\{S1($S_k^i$)\}.

Similar to that of Lemma 5. An algorithm designated herein as Algorithm M3 solves the M3 problem:

Algorithm M3
Compute max$_i$\{S1($P_j^i$)\}+max$_i$\{S1($M_{(j,k)}^i$)\}+max$_i$\{S1($S_k^i$)\}
  for 1<j≦w+1, g−w<k≦g, 0<k−j≦w.
Split the field at two points $x_j$, $x_k$, such that 1<j≦w+1,
  g−w<k≦g, 0<k−j≦w, and max$_i$\{S1($P_j^i$)\}+max$_i$\{S1 ($M_{(j,k)}^i$)\}+max$_i$\{S1($S_k^i$)\} is minimized.

The complexity analysis is similar to that of Algorithm M2. In this case though, O(g$^2$) pairs of split points have to be examined. The time complexity of Algorithm M3 is O(ng$^2$).

Bounds on optimal therapy time ratios for the case of multiple leaf pair is now considered. The following bounds on ratios of optimal therapy times are proven:

Lemma 7.
1≦M2(I)/M1(I)≦2
1≦M3(I)/M1(I)<3
0.5<M3(I)/M2(I)<2

M2(I)=max$_i$\{S1($P_j^i$)\}+max$_i$\{S1($S_j^i$)\}, where j is as determined by Algorithm M2. max$_i$\{S1($P_j^i$)\}+max$_i$\{S1 ($S_j^i$)\}≧max$_i$\{S1($P_j^i$)+S1($S_j^i$)\}≧max$_i$\{S1($I_i$)\}=M1(I). This implies M2(I)/M1(I)≧1 and so splitting a field into two never improves optimal therapy time. For an upper bound on the ratio, note that max$_i$\{S1($P_j^i$)\}≦max$_i$\{S1($I_i$)\} and max$_i$\{S1($S_j^i$)\}≦max$_i$\{S1($I_i$)\}. It follows that M2(I) =max$_i$\{S1($P_j^i$)\}+max$_i$\{S1($S_j^i$)\}≦2*M1(I).

M3(I)=max$_i$\{S1($P_j^i$)\}+max$_i$\{S1($M_{(j,k)}^i$)\}+max$_i$\{S1 ($S_k^i$)\}, where j,k are as in Algorithm M3. The proof that M3(I)/M1 (I)≧1 is similar to that of (a). As in (a), M1(I)≧ each of the three terms in M3(I). Therefore, M3(I)≦3*M1(I).

From above, M3(I)≧M1(I) and M2(I)≦2*M1(I). So M3(I)/M2(I)≧0.5. To obtain an upper bound note that the best split point for M2 (say $x_j$) is always a permissible split point for M3. By selecting this as one of the two split points for M3, split can be constructed into three profiles such that the total therapy time of profiles resulting from this split is max$_i$\{S1($P_j^i$)\}+max$_i$\{S1($M_{(j,k)}^i$)\}+max$_i$\{S($S_k^i$)\}, where k is the second split point defining that split. Since max$_i$\{S1 ($M_{(i,k)}^i$)\}+max$_i$\{S1($S_k^i$)\}≦2*max$_i$\{S1($S_j^i$)\}, it follows that the total therapy time of profiles resulting from this split is max$_i$\{S1($P_j^i$)\}+max$_i$\{S1($M_{(j,k)}^i$)\}+max$_i$\{S1($S_k^i$)\}≦max$_i$\{S1 ($P_j^i$)\}+2*max$_i$\{S1($S_j^i$)\}≦2*M2(I) So M3(I)/M2(I)≦2.

It is noted that the examples used to show tightness of bounds in the proof of Lemma 4 can also be used to show tightness of bounds in this case.

Algorithms M2 and M3 may be extended to generate optimal therapy time fields with elimination of tongue-and-groove under dosage and (optionally) the interdigitation constraint on the leaf sequences. The inventors in U.S. application Ser. No. 10/736,023, incorporated herein, describe algorithms for delivering an intensity matrix I using a single field with optimal therapy time, while eliminating the tongue-and-groove under dosage (according to an algorithm designated herein as Algorithm TONGUEAND-GROOVE) and also while simultaneously eliminating the tongue-and-groove under dosage and interdigitation constraint violations (according to an algorithm designated herein as Algorithm TONGUEANDGROOVE-ID). These problems are denoted by M1' and M1' respectively (M2', M2", M3' and M3" are defined similarly for splits into two and three fields). Let M1'(I) and M1"(I), respectively, denote the optimal therapy times required to deliver I using the leaf sequences generated by these algorithms. To solve problem M2' it is needed to determine $x_j$ where M1'($P_j$)+M1'($S_j$) is minimized for g−w<j≦w+1. Note that this is similar to Algorithm M2. Using the fact that M1' can be solved in O(nm) time for an intensity profile with n rows and m columns, and by computing M1'($P_j$) and M1'($S_j$) progressively from left to right, it is possible to solve M2' in O(ng) time. In case of M3' it is needed to find $x_j$, $x_k$, such that 1<j≦w+1, g−w<k≦g, 0<k−j≦w, and M1'($P_j$)+M1'($M_{(j,k)}$)+M1'($S_k$) is minimized. M3' can be solved in O($ng^2$) time. The solutions for M2" and M3" are now clear.

The invention can be used together with the "feathering" technique known to those having ordinary skill in the art. In this technique, the component beams overlap each other slightly and the intensity gradually decreases for one field component and increases for the other in the overlap region(s). The sum of intensities remains the same as for the original field. This method provides a smooth transition from one field component to the next thereby eliminating, or at least substantially reducing the field junction problem. A preprocessing program, the results of which are used to produce leaf trajectories for each of the component fields, can carry out the beam splitting function.

The present invention is further illustrated by the following specific examples, which should not be construed as limiting the scope or content of the invention in any way.

The performance of the Algorithms M2 and M3 was tested on a Varian Clinac 2100 C/D (Varian Medical, Palo Alto, Calif.) using 12 clinical fluence matrices, each of which exceeded the maximum allowable field width w. The fluence matrices were generated with a commercial inverse treatment planning system (CORVUS v5.0, NOMOS Corp., Sewickley, Pa.) for two clinical cases, one with a 20% fluence step (Table 1) and the other with a 10% fluence step (Table 2). Although tested on a Varian system using a CORVUS planning system, the invention is clearly in no way limited to such systems.

Both algorithms were used whenever the profile width was ≦2w and Algorithm M3 was used when the profile width exceeded 2w. Tables 1 and 2 display the resulting total MUs obtained for the two algorithms. Also shown are the total MUs obtained using the field split lines as given by the commercial treatment planning system (C(I)). The MUs are normalized to give a maximum pixel value of 100 of a fluence map. The percent decrease in MUs of min{M2(I), M3(I)} as a result of optimal field splitting over C(I) is also shown. The average decrease in MUs is found to be about 13% for the 12 fluence matrices.

Figure 11:
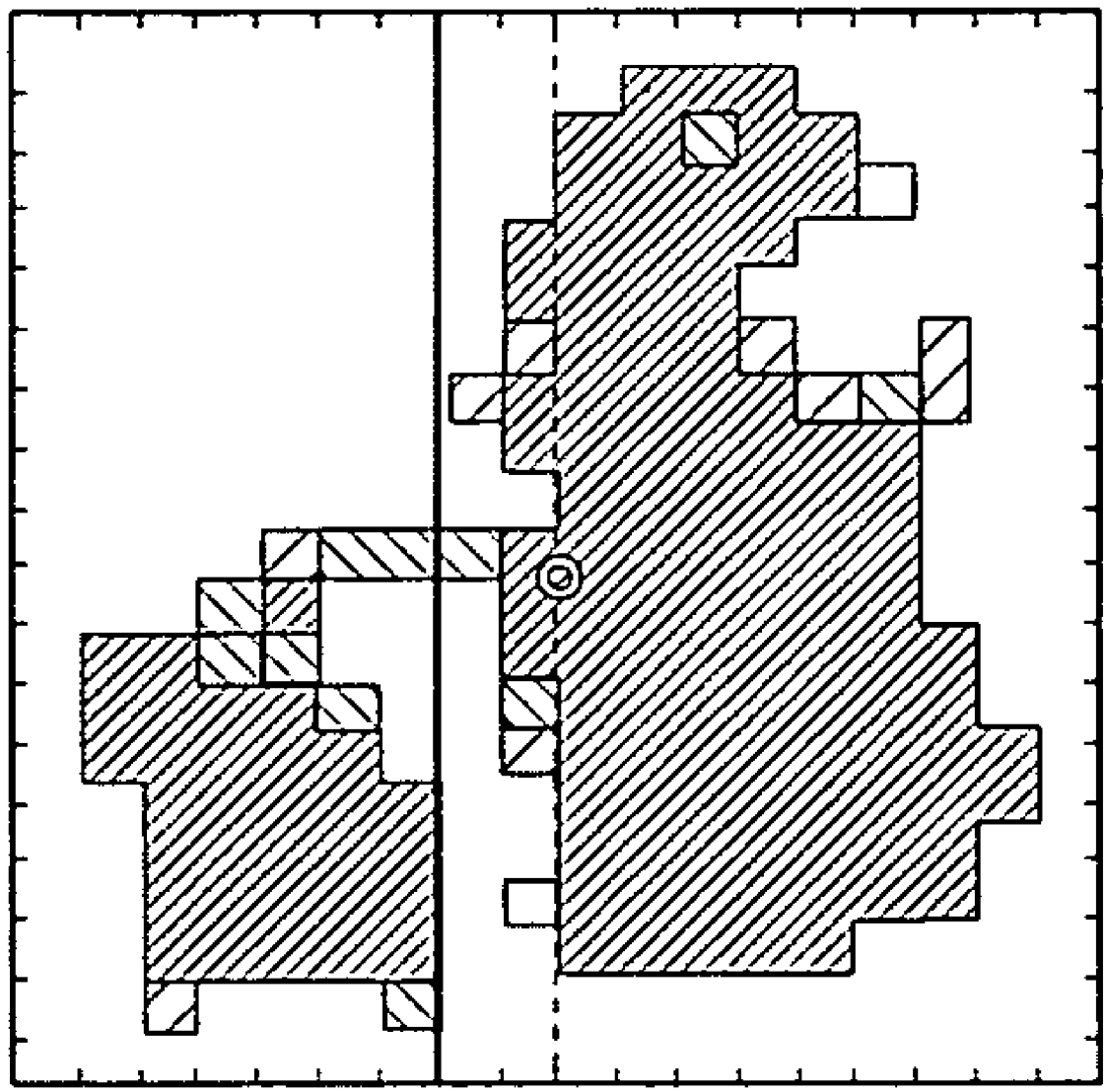
FIG. 11 compares the split line determined according to the invention with that obtained from a commercial planning system for a fluence matrices.

Examination of the optimal split lines using the algorithmic features of the present invention shows that the split lines generally occurred in low fluence columns. FIG. 11 compares the split line from Algorithm M2 and that from the commercial planning system for one of the fluence matrices. The split line from the commercial planning system occurred at the center of the field, whereas a slight shift in the split line reduces the total MU by 10% in this case (Table 2). An added benefit of using optimal field splitting instead of having the split lines always at the center of the field is the automatic feathering.

TABLE 1

Total MUs for the first clinical case

| Matrix (I) | 1 | 2 | 3 | 4 | 5 |
|---|---|---|---|---|---|
| C(I) | 560 | 280 | 560 | 520 | 300 |
| M2(I) | — | 240 | 440 | — | 260 |
| M3(I) | 480 | 260 | 460 | 480 | 340 |
| % MU decrease | 14.2 | 14.3 | 21.4 | 7.7 | 13.3 |

TABLE 2

Total MUs for the second clinical case

| Matrix (I) | 1 | 2 | 3 | 4 | 5 | 6 | 7 |
|---|---|---|---|---|---|---|---|
| C(I) | 280 | 380 | 400 | 350 | 340 | 390 | 350 |
| M2(I) | 280 | 280 | 300 | 350 | 310 | 310 | 320 |
| M3(I) | 330 | 320 | 370 | 380 | 310 | 360 | 340 |
| % MU decrease | 0 | 26.3 | 25.0 | 0 | 9.7 | 20.5 | 9.4 |

One of the problems associated with field splitting is the field matching problem that occurs in the field junction region due to uncertainties in setup and organ motion. To illustrate the problem we use an example. Suppose a field is split at $x_j$. Further suppose that the left field is delivered accurately and that the right field is misaligned so that its left end is positioned at $x_j'$ rather than $x_j$. The region between $x_j'$ and $x_j$ gets overdosed and is a hotspot. The region between $x_j$ and $x_j'$ gets underdosed and is a coldspot.

One way to partially eliminate the field matching problem is to use the 'feathering' technique. According to this technique, the large field is not split at one sample point into two non-overlapping fields. Instead the profiles to be delivered by the two fields resulting from the split, overlap over a central feathering region. The purpose of feathering is to lower the magnitude of maximum intensity error e in the delivered profile from the desired profile over all sample points in the junction region.

In this section, we extend our field splitting algorithms to incorporate feathering. Our feathering scheme is defined for profiles discretized in space and in MUs as is the profile generated by the optimizer. The feathering scheme, moreover defines the profile values in the feathering region, which is centered at some sample point called the split point for that split. Thus given a split point, our scheme will specify how to split the large field with a feathering region that is centered at that point. The split point to be used in the actual split will be determined by a splitting algorithm that takes into account the feathering scheme.

We study how to split a single leaf pair profile into two (three) fields using our feathering scheme such that the sum of the optimal therapy times of the individual fields is minimized. We will denote this minimization problem by S2 F (S3F). The extension of the methods developed for the multiple leaf pairs problems (M2F and M3F) is straightforward and is therefore not discussed separately.

For splitting a profile into two, let I be a single leaf pair profile. Additionally, let $x_j$ be the split point and let $P_j$ and $S_j$ be the profiles resulting from the split. $P_j$ is a left-profile and $S_j$ is a right profile of I. The feathering region spans $x_j$ and d−1 sample points on either side of $x_j$, i.e., the feathering region stretches from $x_{j−d+1}$ to $x_{j+d−1}$. $P_j$ and $S_j$ are defined as follows.

$$P_j(x_i) = \begin{cases} I_j(x_i) & 1 \le i \le j-d \\ \lceil I_j(x_i)*(j+d-i)/2d \rceil & j-d < i < j+d \\ 0 & j+d \le i \le g \end{cases} \quad (1)$$

$$S_j(x_i) = \begin{cases} 0 & 1 \le i \le j-d \\ I_j(x_i) - P_j(x_i) & j-d < i < j+d \\ I_j(x_i) & j+d \le i \le g \end{cases} \quad (2)$$

Note that the profiles overlap over the 2d−1 points j−d+1, j−d+2, . . . , j+d−2, j+d−1. Therefore, for the profile I of width g to be deliverable using two fields, it must be the case that g≤2w−2d+1. Since $P_j$ needs to be delivered using one field, the split point $x_j$ and at least d−1 points to the right of it should be contained in the first field, i.e., j+d−1≤w→j≤w−d+1. Similarly, since $S_j$ has to be delivered using one field j−(d−1)>g−w.→.j≥g−w+d. These range restrictions on j lead to an algorithm for the S2 F problem. Algorithm S2 F, which solves problem S2 F, is described below. Note that the $P_{iS}$ and $P_{iS}$ can all be computed in a single left to right sweep in 0(d) time at each i. So the time complexity of Algorithm S2 F is O(dg).

Algorithm S2 F
(1) Find $P_i$ and $S_i$ using Equations 1 and 2, for g−w+d≤i≤w−d+1.
(2) Split the field at a point $x_j$ where S1($P_j$)+S1($S_j$) is minimized for g−w+d≤j≤w−d+1.

Splitting a profile into three while addressing the matching problem is now considered. Suppose that a profile I is split into three profiles with feathering. Let j and k, j≤k, be the two split points. As a result we get three profiles, $P_j$, $M_{(j,k)}$ and $S_k$, where $P_j$ is a left profile, $M_{(j,k)}$ is a middle profile of I and $S_k$ is a right profile. In this case, there are two feathering regions. each of which spans across 2d−1 sample points centered at the corresponding split point. One feathering region stretches from $x_{j−d+1}$ to $x_{j+d−1}$ and the other form $x_{k−d+1}$ to $x_{k+d−1}$. $P_j$, $M_{(j,k)}$ and $S_j$ are defined as follows.

$$P_j(x_i) = \begin{cases} I_j(x_i) & 1 \le i \le j-d \\ \lceil I_j(x_i)*(j+d-i)/2d \rceil & j-d < i < j+d \\ 0 & j+d \le i \le g \end{cases} \quad (3)$$

$$M_{(j,k)}(x_i) = \begin{cases} 0 & 1 \le i \le j-d \\ I_j(x_i) - P_j(x_i) & j-d < i < j+d \\ I_j(x_i) & j+d \le i \le k-d \\ \lceil I_k(x_i)*(k+d-i)/2d \rceil & k-d < i < k+d \\ 0 & k-d \le i \le g \end{cases} \quad (4)$$

$$S_j(x_i) = \begin{cases} 0 & 1 \le i \le k-d \\ I_j(x_i) - M_{(j,k)}(x_i) & k-d < i < k+d \\ I_j(x_i) & k+d \le i \le g \end{cases} \quad (5)$$

The profiles $P_j$ and $M_{(j,k)}$ overlap over 2d−1 points, as do $M_{(j,k)}$ and $S_k$. For the profile I to be deliverable using three fields, it must be the case that g≤3w−2(2d−1)=3w−4d+2. Also, it is undesirable for the two feathering regions to overlap. So g≥4d−2. For the feathering regions to be well defined and for the split to be useful it can be shown that g−2w+3d−1≤j≤w−d+1 and that g−w+d≤k≤2w−3d+2. Also, k−j+1+2(d−1)≤w→k−j≤w−2d+1. Using these ranges for j and k, we arrive at Algorithm S3F, which can be implemented to solve problem S3F in 0(dg²) time.

Algorithm S3F
(1) Find $P_j$, $M_{(j,k)}$ and $S_k$ for g−2w+3d−1≤j≤w−d+1, g−w+d≤k≤2w−3d+2 and k−j≤w−2d+1.
(2) Split the field at two points $x_j$, $x_k$, where S1($P_j$)+S1($M_{(j,k)}$)+S1($S_j$) is minimized, subject to g−2w+3d−1≤j≤w−d+1, g−w+d≤k≤2w−3d+2 and k−j≤w−2d+1.

Further in the context of the mismatch problem, it remains to consider the tongue-and-groove effect and interdigitation. The algorithms for M2F and M3F may be further extended to generate optimal therapy time fields with elimination of tongue-and-groove underdosage and (optionally) the interdigitation constraint on the leaf sequences as is done for field splits without feathering. The definitions of problems M2F″ (M3F″) and M2F″ (M3F″), respectively, for splits into two (three) fields are similar to those for splits without feathering.

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself.

We claim:

1. A method of delivering intensity-modulated radiation therapy (IMRT), comprising the steps of:
    (a) providing an intensity profile for the treatment of a patient, the intensity profile spanning a prescribed field width and comprising a discrete profile having intensity values at each of a plurality of sample points bounded by the prescribed width;
    (b) comparing the prescribed width to a maximum field width provided by a radiation treatment system;
    (c) splitting the intensity profile into a plurality of intensity profile portions each having respective widths less than the maximum width if the prescribed width is greater than the maximum width, wherein the splitting includes dividing the prescribed field into a plurality of different profile portion split arrangements and calculating a monitor unit (MU) efficiency for each of the plurality of arrangements, and
    (d) selecting one of the arrangements from arrangements having an MU efficiency at least 10% greater as compared to splitting based on equal width intensity profile portions for delivery by the system using a leaf sequencing method.

2. The method of claim 1, wherein the leaf sequencing method is derived from:
    (e) converting a fluence map which provides the intensity profile into a preliminary leaf sequence, wherein the preliminary leaf sequence minimizes machine on-time and is generated without any leaf movement constraints;
    (f) imposing at least one leaf movement constraint on the preliminary leaf sequence, and
    (g) applying at least one constraint elimination algorithm, the algorithm adjusting the preliminary leaf sequence to minimize violations of the constraint while providing the fluence map and the minimized on-time.

3. The method of claim 2, wherein the multi-leaf collimation is segmented multi-leaf collimation.

4. The method of claim 3, wherein the constraint comprises a minimum separation distance between adjacent leaves in the leaf pair, the applying step (g) comprising:
   (h) modifying at least one leaf pair in the preliminary leaf sequence to form a modified leaf sequence, wherein the modifying step comprises identifying and adjusting positions of leaves in the preliminary leaf sequence which violate the minimum separation distance to provide at least the minimum separation distance;
   (i) modifying at least one leaf pair in the modified leaf sequence to produce a further modified leaf sequence, the further modified leaf sequence providing the intensity profile;
   (j) examining the further modified leaf sequence for violations of the minimum separation distance, and
   (k) iteratively repeating the steps (h) and (i) if at least one violation of the minimum separation distance is identified in step (j) using the further modified leaf sequence as the preliminary leaf sequence to generate a corrected leaf sequence.

5. The method of claim 4, further comprising the step of reducing a tongue-and-groove underdose, the step of reducing the tongue-and-groove underdose comprising applying a tongue-and-groove constraint to the corrected leaf sequence, the applying a tongue-and-groove constraint step comprising the steps of:
   (l) modifying at least one leaf pair in the corrected leaf sequence to form a modified corrected leaf sequence, wherein the modifying step comprises identifying and adjusting positions of leaves in the preliminary leaf sequence which violate a tongue-and-groove constraint;
   (m) modifying at least one leaf pair in the modified corrected leaf sequence to produce a further modified leaf sequence, the further modified leaf sequence providing the fluence map;
   (n) examining the further modified corrected leaf sequence for violations of tongue-and-groove constraint, and
   (o) iteratively repeating the steps (l) and (m) if at least one violation of the tongue and groove constraint is identified in step (n) using the further modified leaf sequence as the preliminary leaf sequence.

6. The method of claim 2 wherein the multi-leaf collimation is dynamic multi-leaf collimation.

7. The method of claim 6, wherein the constraint comprises a leaf interdigitation constraint, the applying step (g) comprises:
   (p) modifying at least one leaf pair in the preliminary leaf sequence to form a modified leaf sequence, wherein the modifying step comprises identifying and adjusting positions of leaves in the preliminary leaf sequence which violate the interdigitation constraint;
   (q) modifying at least one leaf pair in the modified leaf sequence to produce a further modified leaf sequence, the further modified leaf sequence providing the fluence map;
   (r) examining the further modified leaf sequence for violations of the interdigitation constraint, and
   (s) iteratively repeating the steps (p) and (q) if at least one violation of the interdigitation constraint is identified in step (r) using the further modified leaf sequence as the preliminary leaf sequence.

8. A system for delivering radiation treatment to a patient, the system comprising:
   a radiation source for providing a radiation beam;
   a beam-shaping device interposed between the radiation source and the patient for shaping the radiation beam, the beam-shaping device having a plurality of leaves that cooperatively form leaf sequences for shaping the radiation beam; and
   a processor in conununication with the beam-shaping device for causing the beam-shaping device to split the radiation beam into a plurality of radiation fields that are delivered to the patient, said processor splitting the intensity profile into a plurality of intensity profile portions each having respective widths less than the maximum width the prescribed width is greater than the maximum width, wherein the splitting includes dividing the prescribed field into a plurality of different profile portion split arrangements and calculating a monitor unit (MU) efficiency for each of the plurality of arrangements, wherein said processor compares the prescribed width to a maximum field width provided by a radiation treatment system and splits the intensity profile into a plurality of intensity profile portions each having respective widths less than the maximum width if the prescribed width is greater than the maximum width, the splitting including dividing the prescribed field into a plurality of different profile portion split arrangements and calculating p monitor unit (MU) efficiency for each of the plurality of arrangements and selecting one of the arrangements for delivery by the system using leaf sequencing method and selecting one of the arrangements from arrangements having an MU efficiency at least 10% greater as compared to splitting based on equal width intensity profile portions for delivery by the system.

9. The system of claim 8, wherein the beam-shaping device is a segmented multi-leaf collimator.

10. The system of claim 8, wherein the beam-shaping device is a dynamic multi-leaf collimator.

11. The system of claim 8, wherein the processor comprises an optimizer for providing an intensity profile for the treatment of a patient, the intensity profile spanning a prescribed field dimension and comprising a discrete profile having intensity values at each of a plurality of sample points bounded by the prescribed dimension.

12. A method of delivering intensity-modulated radiation therapy (IMRT), comprising the steps of:
   (a) providing an intensity profile for the treatment of a patient, the intensity profile spanning a prescribed field width and comprising a discrete profile having intensity values at each of a plurality of sample points bounded by the prescribed width;
   (b) comparing the prescribed width to a maximum field width provided by a radiation treatment system;
   (c) splitting the intensity profile into a plurality of intensity profile portions each having respective widths less than the maximum width if the prescribed width is greater than the maximum width, wherein the splitting includes dividing the prescribed field into a plurality of different profile portion split arrangements using an M2 procedure, and calculating a monitor unit (MU) efficiency for each of the plurality of arrangements; and
   (d) selecting one of the arrangements from arrangements having an MU efficiency at least 10% greater as compared to splitting based on equal width intensity profile portions for delivery by the system using a leaf sequencing method.

13. The method of claim 12, wherein the leaf sequencing method is derived from:

(e) converting a fluence map which provides the intensity profile into a preliminary leaf sequence, wherein the preliminary leaf sequence minimizes machine on-time and is generated without any leaf movement constraints;

(f) imposing at least one leaf movement constraint on the preliminary leaf sequence, and (g) applying at least one constraint elimination algorithm, the algorithm adjusting the preliminary leaf sequence to minimize violations of the constraint while providing the fluence map and the minimized on-time.

14. The method of claim 13, wherein the multi-leaf collimation is segmented multi-leaf collimation.

15. The method of claim 14, wherein the constraint comprises a minimum separation distance between adjacent leaves in the leaf pair, the applying step (g) comprising:

(h) modifying at least one leaf pair in the preliminary leaf sequence to form a modified leaf sequence, wherein the modifying step comprises identifying and adjusting positions of leaves in the preliminary leaf sequence which violate the minimum separation distance to provide at least the minimum separation distance;

(i) modifying at least one leaf pair in the modified leaf sequence to produce a further modified leaf sequence, the further modified leaf sequence providing the intensity profile;

(j) examining the further modified leaf sequence for violations of the minimum separation distance, and (k) iteratively repeating the steps (h) and (i) if at least one violation of the minimum separation distance is identified in step (j) using the further modified leaf sequence as the preliminary leaf sequence to generate a corrected leaf sequence.

* * * * *

UNITED STATES PATENT AND TRADEMARK OFFICE
CERTIFICATE OF CORRECTION

| | |
|---|---|
| PATENT NO. | : 7,142,635 B2 |
| APPLICATION NO. | : 11/102083 |
| DATED | : November 28, 2006 |
| INVENTOR(S) | : Kamath et al. |

It is certified that error appears in the above-identified patent and that said Letters Patent is hereby corrected as shown below:

Claim 8, column 16, line 13, after "maximum width" add --if--.
Claim 8, column 16, line 26, after "calculating" replace "p" with --a--.
Claim 8, column 16, line 29, after "using" add --a--.

Signed and Sealed this

Twenty-third Day of January, 2007

JON W. DUDAS
*Director of the United States Patent and Trademark Office*